United States Patent
Chikkali et al.

(10) Patent No.: US 10,865,174 B2
(45) Date of Patent: Dec. 15, 2020

(54) ONE STEP PROCESS FOR THE HYDROFORMYLATION OF OLEFINS

(71) Applicant: Council of Scientific & Industrial Research, New Delhi (IN)

(72) Inventors: Samir Hujur Chikkali, Maharashtra (IN); Swechchha Pandey, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/610,464

(22) PCT Filed: Apr. 27, 2018

(86) PCT No.: PCT/IN2018/050259
§ 371 (c)(1),
(2) Date: Nov. 1, 2019

(87) PCT Pub. No.: WO2018/203344
PCT Pub. Date: Nov. 8, 2018

(65) Prior Publication Data
US 2020/0148615 A1  May 14, 2020

(30) Foreign Application Priority Data
May 2, 2017 (IN) .............................. 201711015470

(51) Int. Cl.
*C07C 45/50* (2006.01)
*B01J 23/00* (2006.01)
*B01J 23/745* (2006.01)

(52) U.S. Cl.
CPC ........... *C07C 45/505* (2013.01); *B01J 23/745* (2013.01)

(58) Field of Classification Search
CPC ....... C07C 45/50; C07C 45/505; B01J 23/745
See application file for complete search history.

(56) References Cited

U.S. PATENT DOCUMENTS 4,058,556 A  11/1977  Rasp et al.
4,782,188 A  11/1988  Butts

OTHER PUBLICATIONS

International Search Report in International Application No. PCT/IN2018/050259, dated Aug. 23, 2018.
Written Opinion of the International Searching Authority in International Application No. PCT/IN2018/050259, dated Aug. 23, 2018.
Bhanage, BM et al. "Kinetics of hydroformylation of I-dodecene using homogeneous HRh(CO)(PPh3)3 catalyst" Journal of Molecular Catalysis A: Chemical; 1997, 115 (2), pp. 247-257.
Booth et al. "Metal carbonyl chemistry. Part III. Iron pentacarbonyl as a hydroformylation catalyst" J. Chem. Soc. C, 1966, pp. 1447-1449.
Breschi et al. "η6-Cyclohepta-1, 3, 5-triene)(η4-cycloocta-1, 5-diene)iron(0) complex as attractive precursor in catalysis" Journal of Organometallic Chemistry; 2000, 607 (1-2), pp. 57-63.
He, Z. et al. "Synthesis and evaluation of the catalytic properties of homo- and hetero-bimetallic complexes containing bridging diphenylphosphido ligands" Journal of Organometallic Chemistry; 1992, 426 (2), pp. 247-259.
Pospech et al. "Alternative metals for homogeneous catalyzed hydroformylation reactions" Angew Chem Int Ed Engl.; 2013; 52(10); pp. 2852-2872.
Sternberg et al. "Binuclear iron carbonyls and their significance as catalytic intermediates" J. Am. Chem. Soc., 1957, 79 (23), pp. 6116-6121.
Trzeciak et al. "The new organometallic rhodium—iron homogeneous catalytic system for hydroformylation" Topics in Catalysis; 2000, 11 (1-4), pp. 461-468.

*Primary Examiner* — Sikarl A Witherspoon
(74) *Attorney, Agent, or Firm* — Knobbe, Martens, Olson & Bear, LLP

(57) ABSTRACT

A one-step process for hydroformylation of olefins can include iron-catalyzed hydroformylation of olefins. The process can result in the conversion of olefin in the range of 40 to 99%. A reaction mixture includes iron precursor, ligand, substrate and solvent. The reaction mixture can be pressurized with syngas ($CO/H_2$) under constant stirring to obtain a desired aldehyde compound. The ligand can be a monodentate ligand of a phosphines or a phosphite, and the iron precursor can be $[HFe(CO)_4]^-$.

9 Claims, 5 Drawing Sheets

Front Signal
Results

| Retention Time | Area | Area % | Height | Height % |
|---|---|---|---|---|
| 7.254 | 1295618 | 1.53 | 252679 | 4.01 |
| 17.037 | 76812390 | 90.87 | 5280267 | 83.77 |
| 23.411 | 6424519 | 7.60 | 770678 | 12.23 |

| Totals | | | | |
|---|---|---|---|---|
| | 84532527 | 100.00 | 6303624 | 100.00 |

Back Signal
Results

| Retention Time | Area | Area % | Height | Height % |
|---|---|---|---|---|
| 2.051 | 48686364 | 50.43 | 45667088 | 75.85 |
| 4.743 | 13322454 | 13.80 | 5140612 | 8.54 |
| 5.658 | 34526226 | 35.77 | 9396930 | 15.61 |
| Totals | 96535044 | 100.00 | 60204630 | 100.00 |

Back Signal
Results

| Retention Time | Area | Area % | Height | Height % |
|---|---|---|---|---|
| 2.725 | 4471477 | 5.68 | 1368813 | 8.08 |
| 7.029 | 25562508 | 32.47 | 6502004 | 38.37 |
| 8.184 | 48698423 | 61.85 | 9074305 | 53.55 |
| Totals | 78732408 | 100.00 | 16945122 | 100.00 |

ONE STEP PROCESS FOR THE HYDROFORMYLATION OF OLEFINS

FIELD OF THE INVENTION

The present invention relates to a one step process for hydroformylation of olefins. More particularly, the present invention relates to one step iron catalyzed process for hydroformylation of olefins, wherein the conversion of olefin is in the range of 40 to 99%.

BACKGROUND AND PRIOR ART OF THE INVENTION

Transition-metal-catalyzed hydroformylation reaction constitutes one of the most powerful tools to construct C—C bond and represents one of the successful example of homogeneous catalysis on an industrial scale. Discovered by German chemist Otto Roelen, transition metal catalyzed hydroformylation (the "oxo" process) is arguably the world's largest homogeneously catalyzed industrial process with the production of 12 million ton oxo-products per annum. The oxo process is a powerful synthetic tool to convert alkenes into aldehydes with perfect atom economy. It has been extensively utilized to construct an array of chemical intermediates. The first and second generation catalysts developed by BASF and ICI were based on cobalt. However, the cobalt-catalyzed process requires harsh conditions such as 100-350 bars syngas (1:1 mixture of $CO:H_2$) pressure and around 100-200° C. temperature. Widespread academic and industrial research to address this bottleneck led to a rhodium catalyzed low-pressure oxo-process (LPO) (10-60 bars and 80-135° C.), which was developed by Union Carbide and Celanese in the mid-1970s. To date, terminal alkenes, internal alkenes, cyclic olefins and aromatic alkenes have been extensively hydroformylated to pharmaceuticals, fragrances and agrochemicals using the precious rhodium metal. Currently, most of the bulk hydroformylation processes rely on rhodium-based catalysts. The increasing demand and resulting high cost of this precious metal has fueled the quest to discover alternative metals with high abundance. Thus, due to technical superiority, the rhodium-based LPO (low-pressure oxo) is still the state of the art process practiced by industry and roughly 70% of the oxo-products are produced using this process. However, the industry is increasingly being faced with the rocketing prices of rhodium due to the high demand of this metal in the automotive industry, which consumes about 80% of this metal. In addition, the natural abundance of this trace element is posing an even bigger challenge and the search for alternative metals has already begun. Thus, iron (Fe) can serve as an alternative to this precious metal because of its low cost & high abundance.

A review Article titled "Alternative metals for homogeneous catalyzed hydroformylation reactions" by J Pospech et al. published in *Angew Chem Int Ed Engl.;* 2013; 52(10); pp 2852-72 reports transition-metal-catalyzed hydroformylation reactions. The review summarizes the progress achieved utilizing Ru, Ir, Pd, Pt, and Fe catalysts in hydroformylation reactions.

Article titled "(η6-Cyclohepta-1, 3, 5-triene)(η4-cycloocta-1, 5-diene)iron(0) complex as attractive precursor in catalysis" by C Breschi et al. published in *Journal of Organometallic Chemistry;* 2000, 607 (1-2), pp 57-63 reports hydroformylation of 1-hexene and styrene and the cyclotrimerisation of a wide range of terminal and internal acetylenes using $Fe(\eta^6\text{-CHT})(\eta^4\text{-COD})$, (CHT=1, 3, 5-cycloheptatriene; COD=1, 5-cyclooctadiene) complex.

Article titled "Synthesis and evaluation of the catalytic properties of homo- and hetero-bimetallic complexes containing bridging diphenylphosphido ligands" by Z He et al. published in *Journal of Organometallic Chemistry;* 1992, 426 (2), pp 247-259 reports the complexes, along with [(CO), Fe(~-PPh,), Fe(CO)], [(PPh)Pd(p-PPh), W(CO),], and [(PPh)Pt(p-PPh), $W(CO)_4$], and these are screened as catalyst precursors for (i) the hydroformylation of styrene (120° C., 20 bar, $CO/H_2$=1), and (ii) the hydrogenation of cyclohexanone (140° C., 40 bar H).

U.S. Pat. No. 4,633,021A discloses a process for the hydroformylation of olefins for the preparation of aldehydes, by reacting carbon monoxide and hydrogen with an olefin, in the presence of an ionic metal complex catalyst where the ionic charge is on either the metal or on a ligand, at a temperature in the range of between about 80° and about 300° C. and a pressure in the range of between about 400 and about 2000 psig, the improvement comprising performing the reaction in a polar solvent selected from the group consisting of N-substituted amides, glycols, polyglycols, mono lower alkyl ethers of glycols, dimethyl sulfoxide and sulfolane and recovering the aldehyde by extraction with a hydrocarbon solvent.

Article titled "Metal carbonyl chemistry. Part III. Iron pentacarbonyl as a hydroformylation catalyst" by BL Booth et al. published in *J. Chem. Soc. C,* 1966, 0, 1447-1449 reports that Iron pentacarbonyl is a poor hydroformylation catalyst, and gives only 17% conversion of ethylene to propionaldehyde and n-propanol under normal hydroformylation conditions. The catalytic system is formed from the mixture of cobalt salts (formates or carbonates) and iron pentacarbonyl. Addition of $Fe(C))_5$ to $CoCO_3$ caused increase of propene conversion and that of $C_4$-aldehydes from 30 to 71%.

Article titled "The new organometallic rhodium-iron homogeneous catalytic system for hydroformylation" by A M Trzeciak et al. published in *Topics in Catalysis;* 2000, 11 (1-4), pp 461-468 reports that the addition of $Fe(CO)_5$ to the systems with [Rh(acac)(CO)L] complexes (L=$PPh_3$, P(OPh)$_3$, P(NC$_4$H$_4$)$_3$) as catalyst precursors caused the increase of aldehydes yield in 1-hexene hydroformylation reaction (80° C., 10 atm) up to 71%.

Article titled "Kinetics of hydroformylation of 1-dodecene using homogeneous HRh(CO) $(PPh_3)_3$ catalyst" by B M Bhanage et al. published in *Journal of Molecular Catalysis A: Chemical;* 1997, 115 (2), pp 247-257 reports the kinetics of the $HRh(CO(PPh_3)_3$ catalyzed hydroformylation of 1-dodecene investigated in a temperature range of 323-343, K. The effect of 1-dodecene and catalyst concentration, $P_H$ and $P_{CO}$, on the rate of reaction has been studied.

Article titled "Binuclear iron carbonyls and their significance as catalytic intermediates" by H W Sternberg et al. published in *J. Am. Chem. Soc.,* 1957, 79 (23), pp 6116-6121 reports the chemical and catalytic properties of solutions obtained by treating $Fe(CO)_5$ with aqueous alkali. In addition, it is shown that iron hydrocarbonyl, $H_2Fe(CO)_4$ also possesses reducing properties and catalyzes the isomerization of double bonds. These properties probably are due to the formation of a binuclear intermediate:

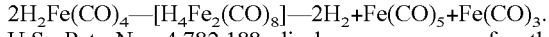

U.S. Pat. No. 4,782,188 discloses a process for the hydroformylation of $C_{2-4}$ alkenes, formyl-substituted $C_{2-4}$ alkenes, aryl-substituted alkenes, unsaturated norbornane ring-containing compounds, and α-unsaturated acetals which comprises contacting a $C_{2-4}$ alkene, a formyl-substituted $C_{2-4}$ alkene, aryl-substituted alkene, an unsaturated norbornane ring-containing compound or an α-unsaturated acetal in a polar organic solvent with water and carbon monoxide in the presence of a catalytic amount of a catalyst which comprises a mixture of (a) an alkali metal iron carbonyl or alkaline earth metal iron carbonyl or a mixture thereof which corresponds to the formula $M_aFe_x(CO)_y$ and (b) iron pentacarbonyl under conditions such that an alcohol or aldehyde derivative of a $C_{2-4}$ alkene, a formyl-substituted $C_{2-4}$ alkene, an aryl-substituted alkene, unsaturated norbornane ring-containing compound or an α-unsaturated acetal, is prepared wherein M is an alkali metal or alkaline earth metal; a is 1 or 2; x is an integer of 2 to 4, inclusive; and y is 8, 11 or 13.

U.S. Pat. No. 4,306,084 discloses to the production of aldehydes and alcohols from olefins and more specifically to the production of normal alcohols from the reaction of olefins, carbon monoxide and water or hydrogen in the presence of a ruthenium carbonyl catalyst. In the Reppe modification, the same conversion is achieved without the use of molecular hydrogen by reaction of the olefin with carbon monoxide and water in the presence of an iron carbonyl catalyst together with a Bronsted or Lewis base. This result was unexpected because iron carbonyl is a very poor catalyst for the hydroformylation reaction in gaseous hydrogen, whereas, under Reppe's conditions, i.e., with $H_2$, O and CO, iron carbonyl becomes an active catalyst at relatively mild temperatures and pressures, i.e. 100° C. and 500 psi.

Later on the field was evolved in terms of applicability of mixed iron-metal clusters for hydroformylation reactions. But in such cases catalyst degradation was the major problem. The Turn over number (TON) was very low. Therefore, to overcome the drawback of prior art: such as catalyst degradation in case of metal clusters as catalyst, use of water gas shift reaction for carbonylating the olefins and formation of alcohols due to reduction of formed aldehyde by in-situ generated $H_2$, poor conversion and regioselectivity, and costly catalysts used. There is need for a simple, efficient, environment friendly and economical process for the synthesis of aldehyde compound. Accordingly, the present invention provides one step Iron catalyzed process for the hydroformylation of olefins.

OBJECTIVE OF THE INVENTION

The main objective of the present invention is to provide a one step process for hydroformylation of olefins.

SUMMARY OF THE INVENTION

Accordingly, the present invention provides a one step process for hydroformylation of olefin comprises charging iron precursor, ligand, olefin and solvent in a reaction vessel followed by pressurizing the reaction mixture with syngas (CO/$H_2$) under constant stirring at temperature in the range of 70 to 100° C. for the period in the range of 16 to 48 hrs to afford desired aldehyde compound, wherein the conversion of said olefin is in the range of 40 to 99%.

In a preferred embodiment, the iron precursor is [HFe(CO)$_4$]$^-$.

In another preferred embodiment, the pressure of the syngas (CO/$H_2$) is in the range of 10 to 30 bars.

The process may optionally comprise addition of acid to the reaction mixture; preferably the acid is selected from acetic acid or formic acid.

The ligand is selected from group consisting of monodentate ligands preferably phosphines or phosphites, more preferably Triphenylphosphine (PPh$_3$) or Triphenyl phosphite [P(OPh)$_3$].

The solvent is selected from protic solvents, wherein the protic solvent is selected from group consisting of methanol, ethanol, isopropyl alcohol, and acetic acid.

The olefin is selected from linear olefin or terminal olefin or internal olefin. More preferably, the olefin is selected from group consisting of 1-hexene, 1-octene, 1-decene, 1-dodecene, 1-octadecene, trimethoxy(vinyl)silane, trimethyl(vinyl)silane, cardanol, 2, 3-dihydrofuran, allyl malonic acid, styrene, 4-methyl styrene, 4-iBu-styrene, 4-tBu-styrene, 4-methoxy styrene, 4-acetoxy styrene, 4-bromo styrene, 4-chloro styrene, 4-vinylbenzonitrile, 4-vinylbenzoic acid, and allyl benzene.

The reaction is carried out in stainless steel autoclave equipped with pressure regulator and an employed safety valve.

The reaction is carried out in batch mode or continuous mode of operation.

Abbreviations

[Fe(CO)$_5$]—Iron pentacarbonyl
[Fe(CO)$_3$(bda)]—(Benzylideneacetone)iron tricarbonyl
[(Ph$_3$P)$_2$—N]$^+$[HFe(CO)$_4$]—Bis(triphenylphosphine)iminium salt of tetracarbonylhydrido ferrate
[(Ph$_3$P)$_2$N]$^+$Cl—Bis(triphenylphosphine)iminium chloride

DETAILED DESCRIPTION OF THE INVENTION

Figure 1:
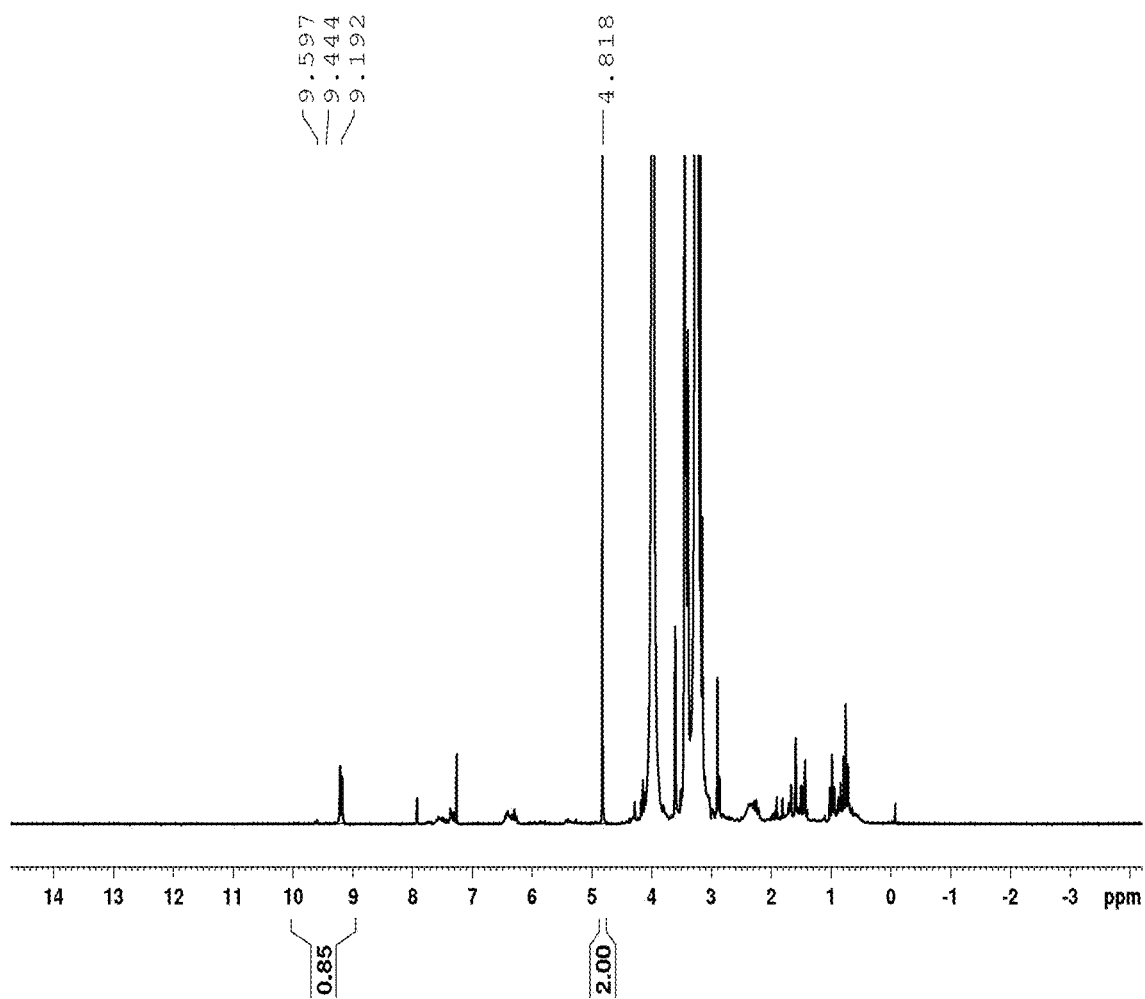
FIG. 1: $^1$H NMR Spectrum of reaction mixture in CDCl$_3$ showing peak for aldehydes in case of (trimethoxy)vinylsilane.

The invention will now be described in detail in connection with certain preferred and optional embodiments, so that various aspects thereof may be more fully understood and appreciated.

In an embodiment, the present invention provides a one step process for the hydroformylation of olefin comprises charging iron precursor, ligand, olefin and solvent in a reaction vessel followed by pressurizing the reaction mixture with syngas (CO/$H_2$) under constant stirring at temperature in the range of 70 to 100° C. for the period in the range of 16 to 48 hrs to afford desired aldehyde compound.

In a preferred embodiment, the conversion of the olefin is in the range of 40 to 99%.

In another preferred embodiment, the iron precursor is [HFe(CO)$_4$]$^-$ and the ligand is selected from group consisting of monodentate ligands preferably phosphines and phosphites, more preferably Triphenylphosphine (PPh$_3$) or Triphenyl phosphite [P(OPh)$_3$].

The solvent is selected from protic solvents, wherein the protic solvent is selected from group consisting of methanol, ethanol, isopropyl alcohol, and acetic acid.

The reaction is carried out in stainless steel autoclave equipped with pressure regulator and an employed safety valve. The autoclave is charged with iron precursor, ligand, solvent, olefin along with teflon stirring bars. In preferred embodiment, before starting the catalytic reaction said charged autoclave is purged three to four times with syngas (CO: $H_2$=1:1) and pressurizing to the desired pressure in the range of 10 bar to 30 bars.

The process may optionally comprise addition of acid to the reaction mixture, wherein the acid is selected from acetic acid or formic acid.

The olefin is selected from linear olefin or terminal olefin or internalolefin. More preferably, the olefin is selected from group consisting of 1-hexene, 1-octene, 1-decene, 1-dodecene, 1-octadecene, trimethoxy(vinyl)silane, trimethyl(vinyl)silane, cardanol, 2, 3-dihydrofuran, allyl malonic acid, styrene, 4-methyl styrene, 4-iBu-styrene, 4-tBu-styrene, 4-methoxy styrene, 4-acetoxy styrene, 4-bromo styrene, 4-chloro styrene, 4-vinylbenzonitrile, 4-vinylbenzoic acid and allyl benzene.

The reaction is carried out in either batch mode or continuous mode of operation.

The hydroformylation of various α olefins using [HFe$(CO)_4$]$^-$ as shown in following scheme 1:

Scheme: 3

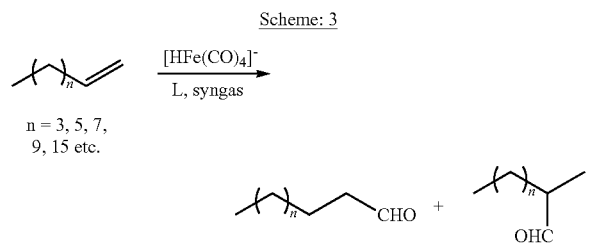

n = 3, 5, 7, 9, 15 etc.

The scope of the iron catalyzed hydroformylation is examined and about 20 substrates are evaluated. Both aliphatic and aromatic substrates are hydroformylated with good to excellent conversion to aldehydes. The aromatic substrates exhibited slightly lower reactivity. A short chain olefin, 1-hexene, is hydroformylated under further milder conditions with 50% exclusive conversion to heptanal along with 72% linear selectivity. Hydroformylation of long-chain olefins is even more challenging, as their reactivity decreases with increasing carbon number and the possibility of internal isomers and corresponding aldehyde products increases. With increasing chain length of the olefin, the reactivity is found to decrease. Thus, at 15 bars syngas pressure and 100° C., a C10 olefin 1-decene led to only 47% yield, whereas increasing the CO/$H_2$ pressure to 30 bars led to an improved yield of 97%. Along the same lines, 1-dodecene and 1-octadecene displayed 97% and 87% yield respectively under identical conditions.

The catalyst is further examined by subjecting functional olefins to iron catalyzed hydroformylation. The catalyst is found to tolerate trimethoxy group without any hindrance and 75% conversion to aldehyde is observed. A slight change in the silane to trimethyl(vinyl)silane led to 49% conversion to aldehyde. A cardanol, which is a non-edible plant oil derived substrate, is tested in the iron catalyzed hydroformylation. Although only 11% aldehyde product could be observed, the fact that such a mixture (cardanol is mixture of three different internal olefins) could be hydroformylated indicates the potential that the iron catalyst holds. A highly challenging heterocyclic olefin, 2, 3-dihydrofuran, is hydroformylated to yield (62%) a highly regioseletive 3-carbaldehyde with 97% selectivity. Hydroformylation of 1, 1-disubstituted difunctional olefin allyl malonic acid lead to reduced activity and only 10% aldehyde could be observed, clearly indicating the limited functional group tolerance of the current catalytic system. On an average, aliphatic olefins are hydroformylated in 24 hours, whereas aromatic substrates required 48 or more hours. Styrene is chosen as a representative benchmark substrate and iron catalyzed hydroformylation is examined, a quantitative conversion is observed at 20 bars syngas pressure at 100° C., with the preferred branched aldehyde formed with 92% selectivity. The reversal of regioselectivity is very commonly observed in styrenic substrates and monodentate phosphine ligands are known to preferably deliver the branched product. Both electron donating and electron withdrawing substituents are tolerated. The electron donating substrates 4-methyl styrene, 4-tertbutyl styrene demanded 30 bars syngas pressure for 45-50% conversion.

The results for the hydroformylation of various olefins using [HFe$(CO)_4$]$^-$ (via in-situ generated catalyst in presence of different ligands as catalyst are presented in table 1 and 2 below:

TABLE 1

Iron (1) catalyzed hydroformylation of 1-octene in the presence of L1$^a$

| Run | L (equiv.) | Solvent | CO/$H_2$ (bars) | Time (h) | Conv. (%)$^b$ | L:B$^b$ |
|---|---|---|---|---|---|---|
| 1 | L1 (1) | MeOH | 20 | 24 | 47 | 73:27 |
| 2 | L1 (2.5) | MeOH | 20 | 24 | 95 | 66:34 |
| 3 | L1 (3) | MeOH | 20 | 24 | 95 | 64:36 |
| 4 | L1 (4) | MeOH | 20 | 24 | 92 | 64:36 |
| 5 | L1 (2.5) | THF | 20 | 24 | 3 | NA |
| 6 | L1 (2.5) | DXN | 20 | 24 | 66 | 73:27 |
| 7 | L1 (2.5) | DCM | 20 | 24 | 24 | 63:37 |
| 8 | L1 (2.5) | EtOH | 20 | 24 | 17 | 67:33 |
| 9 | L1 (2.5) | iPrOH | 20 | 24 | 20 | 70:30 |
| 10 | L1(2.5) | MeOH | 30 | 48 | 90 | 60:40 |
| 11 | L1(2.5) | MeOH | 30 | 24 | 76 | 70:30 |
| 12 | L1(2.5) | MeOH | 15 | 24 | 62 | 67:33 |
| 13$^c$ | L1(2.5) | MeOH | 20 | 24 | 85 | 67:33 |
| 14$^d$ | L1(2.5) | MeOH | 20 | 24 | 3 | 74:26 |
| 15 | NA | MeOH | 35 | 24 | 0 | NA |
| 16 | L2(1) | MeOH | 20 | 48 | 18 | 68:32 |
| 17 | L2(2.5) | MeOH | 20 | 48 | 47 | 70:30 |
| 18 | L2(3) | MeOH | 20 | 48 | 27 | 65:35 |
| 19 | L2(2.5) | MeOH | 30 | 48 | 92 | 63:37 |
| 20 | L2(2.5) | MeOH | 30 | 24 | 5 | 76:24 |
| 21 | L2(2.5) | MeOH | 20 | 24 | 2 | NA |
| 22$^e$ | L2(2.5) | MeOH | 20 | 24 | 23 | 68:32 |

$^a$Conditions: 1: 0.0077 mmol, Ligand/Metal: 2.5, L1 = PPh$_3$, L2 = P(OPh)$_3$; Sub/Fe: 100, Solvent: 1 ml, NA: Not applicable; MeOH—Methanol, THF—Tetrahydrofuran, DXN—1,4-dioxane, DCM—Dichloromethane, EtOH—Ethanol, iPrOH—Isopropanol, hardly any (~1%) hydrogenation product was detected.
$^b$Determined by GC.
$^c$Performed at 120° C.
$^d$Performed at 80° C.
$^e$L2 was incubated for 24 hours before addition of 1-octene.

TABLE 2

Iron (1) catalyzed hydroformylation of alkenes in the presence of L1$^a$

| Run | Substrate | Temp. (° C.) | CO/$H_2$ (bars) | Time (h) | Conv. (%)b | L:B $^b$ |
|---|---|---|---|---|---|---|
| 1 | S2 | 80 | 10 | 48 | 50 | 72:28 |
| 2 | S3 | 100 | 30 | 24 | 97 | 61:39 |
| 3 | S4 | 100 | 30 | 24 | 97 | 61:39 |
| 4 | S5 | 100 | 30 | 24 | 87 | 48:52 |

TABLE 2-continued

Iron (1) catalyzed hydroformylation of alkenes in the presence of L1[a]

| Run | Substrate | Temp. (° C.) | CO/H$_2$ (bars) | Time (h) | Conv. (%)b | L:B [b] |
|---|---|---|---|---|---|---|
| 5 | S6[c] | 100 | 30 | 24 | 75 | 5:95 |
| 6[d] | S7[c] | 100 | 30 | 24 | 99 | 67:33 |
| 7[e] | S8[c] | 100 | 30 | 48 | 43 | 45:55 |
| 8 | S9 | 70 | 25 | 24 | 62 | 3:97 |
| 9[f] | S10[c] | 100 | 30 | 48 | 82 | 50:50 |
| 10 | S11 | 100 | 20 | 48 | 99 | 8:92 |
| 11 | S12 | 100 | 30 | 48 | 45 | 13:87 |
| 12 | S13 | 100 | 30 | 48 | 15 | 28:72 |
| 13 | S14 | 100 | 30 | 48 | 46 | 7:93 |
| 14 | S15 | 100 | 30 | 48 | 96 | 11:89 |
| 15 | S16 | 100 | 25 | 48 | 68 | 2:98 |
| 16 | S17 | 100 | 20 | 48 | 97 | 4:96 |
| 17 | S18 | 100 | 30 | 48 | 72 | 8:92 |
| 18 | S19 | 100 | 25 | 48 | 19 | 10:90 |
| 19[g] | S20[c] | 100 | 30 | 48 | 99 | 0:99 |
| 20 | S21 | 100 | 35 | 48 | 22 | 64:36 |

[a]Conditions: 1: 0.0077 mmol, Ligand/Metal: 2.5, Sub/Fe: 100, Solvent: 1 ml methanol; S2: 1-hexene, S3: 1-decene, S4: 1-dodecene, S5: 1-octadecene, S6: trimethoxy(vinyl) silane, S7: trimethyl(vinyl)silane, S8: Cardanol, S9: 2,3-dihydrofuran, S10: Allyl malonic acid, S11: styrene, S12: 4-methyl styrene, S13: 4-iBu-styrene, S14: 4-tBu-styrene, S15: 4-methoxy styrene, S16: 4-acetoxy styrene, S17: 4-bromo styrene, S18: 4-chloro styrene, S19: 4-vinylbenzonitrile, S20: 4-vinylbenzoic acid, S21: allyl benzene; NA: Not applicable
[b] Determined by GC.
[c]Yields determined by $^1$H NMR with CH$_2$Br$_2$ as an internal standard,
[d]conversion to aldehyde is 49%;
[e]conversion to aldehyde is 11%;
[f]conversion to aldehyde is 10%;
[g]conversion to aldehyde is 26%.

In one embodiment of the present invention, the process may optionally addition of acid to the reaction mixture; preferably the acid is selected from acetic acid or formic acid.

The results of acetic acid promoted iron {[HFe(CO)$_4$]—[PPN]+} catalyzed hydroformylation 1-hexene, styrene, 4-methoxy styrene and 4-methyl styrene are presented in table 3 below:

TABLE 3

Acetic acid promoted iron (1) catalyzed hydroformylation of 1-hexene, styrene, 4- methoxy styrene and 4-methyl styrene[a]

| Sr. No. | Substrate | AcOH (equiv.) b | CO/H$_2$ bars | Time (h) | Conv. (%)c | L:Bc |
|---|---|---|---|---|---|---|
| 1 | 1-hexene | 1 | 20 | 16 | 49 | 72:28 |
| 2 | 1-hexene | 2 | 20 | 16 | 25 | 73:27 |
| 3 | 1-hexene | 5 | 20 | 16 | 1 | NA |
| 4 | styrene | 1 | 20 | 24 | 94 | 14:76 |
| 5 | 4-methoxy styrene | 1 | 20 | 24 | 32 | 16:84 |
| 6 | 4-methyl styrene | 1 | 20 | 24 | 64 | 16:84 |
| 7 | 4-methoxy styrene | 1 | 20 | 24 | 80 | 8:92 |

[a]Conditions: 1-0.0077 mmol, Ligand/Metal: 2.5, Sub/Fe: 100, Solvent: 1 ml Methanol, NA: Not determined,
b equivalent of acetic acid as compared to the catalyst,
cDetermined by GC.

FIG. 1 shows $^1$H NMR Spectrum of reaction mixture in CDCl$_3$ showing peak for aldehydes in case of (trimethoxy) vinylsilane.

Figure 2:
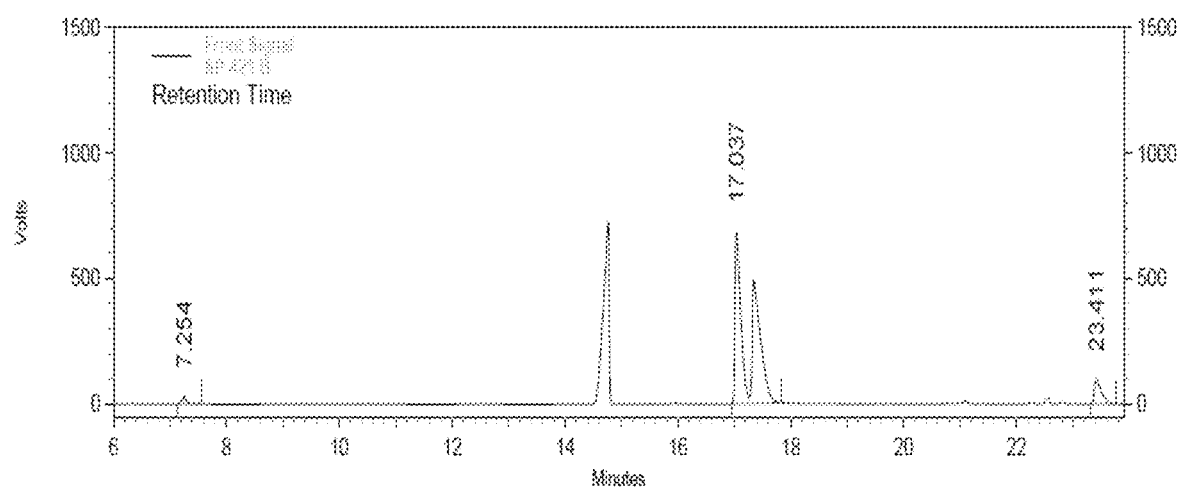
FIG. 2: GC chromatogram for Hydroformylation of styrene showing regioselectivity 8:92.

FIG. 2 shows GC chromatogram for HF of styrene showing regioselectivity 8:92.

EXAMPLES

Following examples are given by way of illustration therefore should not be construed to limit the scope of the invention.

Example 1

Synthesis of Iron Complexes [Fe(CO)$_5$] and [HFe(CO)4]−[PPN]+

We began with the synthesis of [Fe(CO)$_5$] following a known literature procedure. 42.01 g (0.0137 mol) of benzylideneacetone, 5 g (0.0137 mol) of [Fe$_2$(CO)$_9$] were suspended in dry toluene (30 ml) in a Schlenk flask. The above suspension was heated at 60° C. for 5 hours, after which volatiles were evaporated under vacuum. The resultant volatiles were collected and subjected to low temperature precipitation at −45° C. to obtain [Fe(CO)$_5$] as straw yellow colored precipitate. The supernatant toluene was syringed out and the resultant solid (64% yield) was used for next step. Subsequently, the solid was allowed to warm up to room temperature, leading to a straw yellow color liquid.

5 g (0.0255 mol) of [Fe(CO)$_5$] was treated with 2.86 g (0.051 mol) of KOH in methanol (40 ml) to obtained the desired metal precursor [HFe(CO)4]−[K]+. 2 A saturated solution of bis-triphenylphosphine iminium chloride (1 g in 10 ml methanol) was added to above [HFe(CO)$_4$]−[K]+ salt to obtain pale yellow colored precipitate. The thus obtained precipitate was further recrystallized from 1:1 hot solution of ethanol:ethyl acetate to obtain [HFe(CO)$_4$]−[PPN]+(1) [where [PPN]+=Bis(triphenylphosphine)iminium cation] in 46% yield.

$^1$H NMR (500 MHz in CD$_3$OD): δ=−8.52 (s, 1H, Fe—H). $^{13}$C NMR (125 MHz in CD$_3$OD): δ=161.5 (C═O), 135.0, 133.6, 130.8, 128.3.31P NMR (500 MHz in CD$_3$OD): δ=21.02. IR (cm$^{-1}$)=1870 (C═O). ESI-MS (-ve mode): m/z=168.91 [M]−.

Example 2

General Procedure for Hydroformylation

In a typical hydroformylation experiment a stainless steel autoclave (450 mL) equipped with 50 ml high pressure liquid charging chamber, pressure regulator and a safety valve was used. Individual vials were charged with metal precursor [HFe(CO)$_4$]−[PPN]+(1) (5.5 mg, 0.0077 mmol), ligand (as in Table 1-3), solvent (1 ml), substrate (100 equiv.) and stirring bars in a glove box. The vials were transferred to autoclave and the autoclave was purged three times with syngas (CO:H$_2$=1:1) before pressurizing it to the desired pressure. Suitable temperature and pressure was maintained during the reaction. After completion of the reaction, the autoclave was cooled to 0° C., and excess gas was vented off in a well-ventilated fume-hood. The conversion and regio-selectivity were determined by using gas chromatography (GC).

Figure 3:
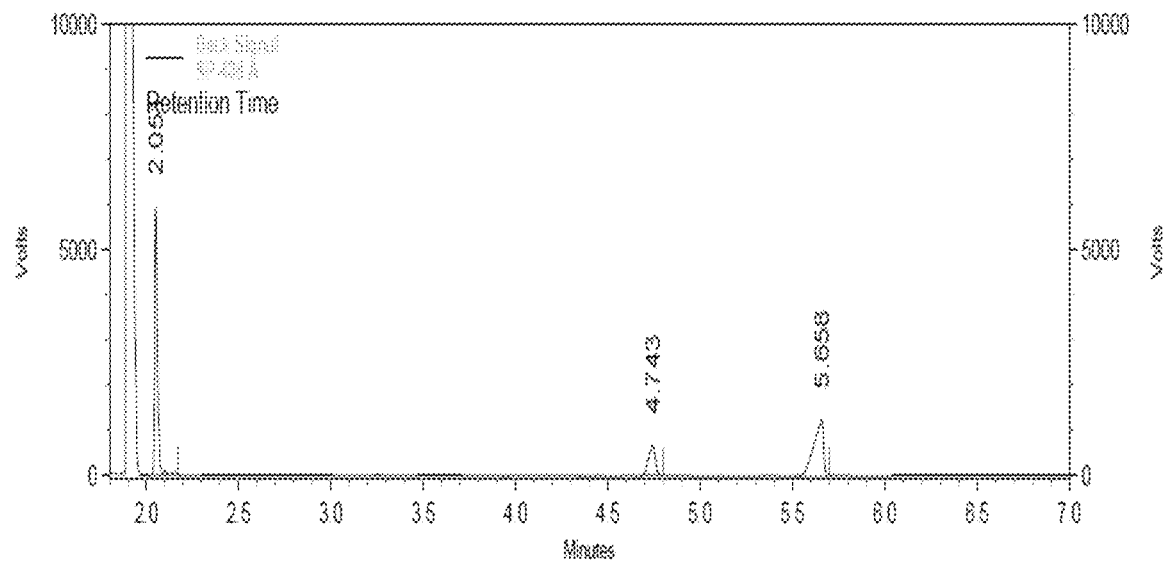
FIG. 3: GC chromatogram of 1-hexene

The results for the hydroformylation of various olefins using [HFe(CO)$_4$]− in presence of different ligands as catalyst are presented in table 1 and 2 below:

1-hexene. GC analysis for 1-hexene was carried out on an Agilent 7890B GC system using HP-05 column (30 m×320 μm×0.25 μm), split ratio 30:1, column pressure 10 psi, injector temperature of 260° C., detector temperature of 330° C., argon carrier gas. Temperature program: Initial temperature 50° C., hold for 1 min.; ramp 1:4° C./min. to 120° C.; ramp 2:20° C./min. to 250° C.; ramp 3:20° C./min. to 320° C., hold for 2 min. Retention time for 1-hexene=2.05 min hydrogenated product (n-hexane)=2.07 min.; branched aldehydes=4.74 min.; linear aldehyde=5.65 minute. (FIG. 3)

Figure 4:
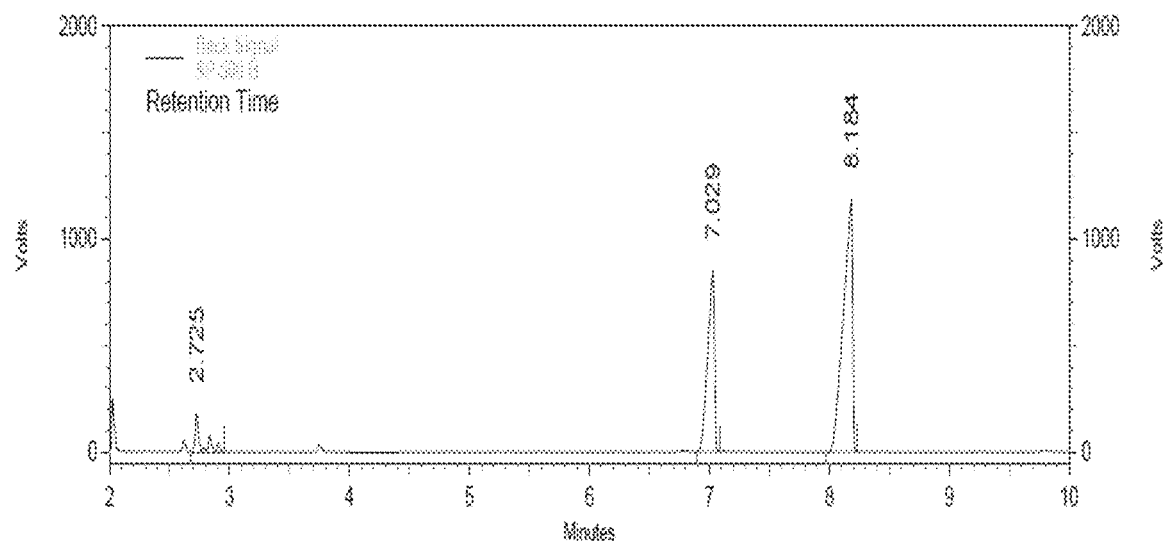
FIG. 4: GC chromatogram of 1-octene

1-octene. Temperature program: Initial temperature 70° C., hold for 1 min.; ramp 1: 4° C./min. to 120° C.; ramp 2:

10° C./min. to 250° C.; ramp 3: 20° C./min. to 320° C., hold for 2 min. Retention time for 1-octene=2.7 min.; hydrogenated product (n-octane)=2.8 min.; branched aldehydes=7.02 min.; linear aldehyde=8.1 minute. (FIG. 4)

Figure 5:
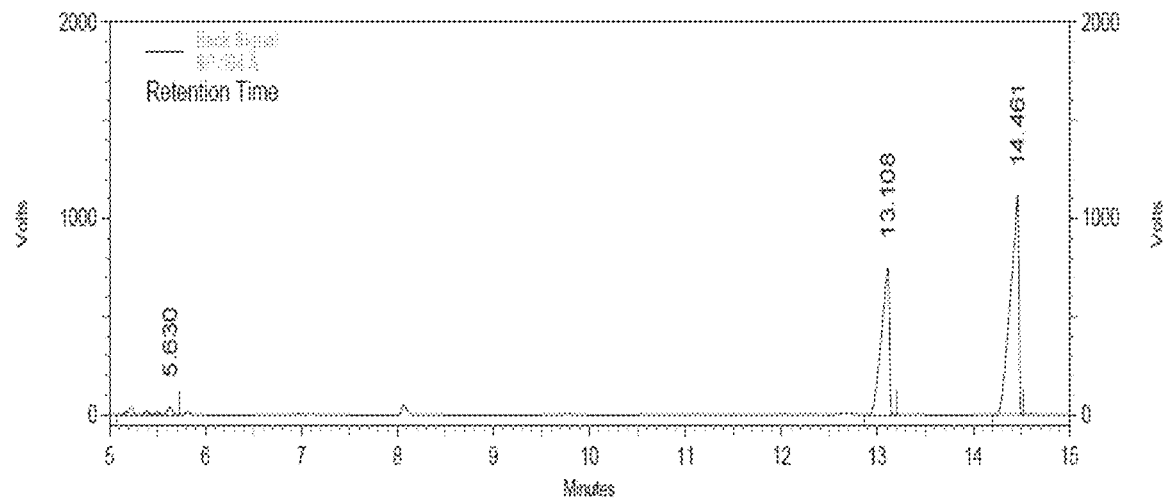
FIG. 5: GC chromatogram of 1-decene

1-decene, 1-dodecene, 1-octadecene. Temperature program: Initial temperature 70° C., hold for 1 min.; ramp 1: 4° C./min. to 120° C.; ramp 2: 10° C./min. to 250° C.; ramp 3: 20° C./min. to 320° C., hold for 2 min. Retention time for 1-decene=5.4 min. hydrogenated product (n-decane)=5.7 min.; branched aldehydes=13.1 min.; linear aldehyde=14.4 minute (FIG. 5). Retention time for 1-dodecene=9.9 min. hydrogenated product (n-dodecane)=11.2 min.; branched aldehydes=18.0 min.; linear aldehyde=18.8 min. Retention time for 1-octadecene=22.4 min.; branched aldehydes=26.0 min.; linear aldehyde=26.5 min.

Styrene, 4-methyl styrene. GC analysis for styrene and 4-methyl styrene was carried out on an Agilent 7890B GC system using Supelco β-dex 225 (30 m*0.25 mm*0.25 μm), split ratio 30:1, column pressure 10 psi., injector temperature of 220° C., detector temperature of 300° C., argon carrier gas. Temperature program: Initial temperature 100° C., hold for 2 min.; ramp 1: 2° C./min. to 160° C.; ramp 2: 20° C./min. to 210° C.; hold for 2 min. Retention time $R_t$ for styrene=7.3 mins. for hydrogenated product (Ethyl benzene) =6.3 mins, n-dodecane=14.7 min. (internal standard), for branched aldehydes=17.0 mins. for linear aldehyde=23.2 mins. Retention time $R_t$ for 4-methylstyrene=10.3 mins. for branched aldehydes=22.0 mins. for linear aldehyde=22.7 mins.

4-methoxy styrene, 4-bromo styrene, 4-iBu-styrene, 4-tBu-styrene, 4-acetoxy styrene, 4-bromo styrene, 4-chloro styrene, 4-vinylbenzonitrile and allyl benzene.

GC analyses for above styrenic substrates was carried out on an Agilent 7890B GC system using Supelco β-dex 225 (30 m*0.25 mm*0.25 μm), split ratio 30:1, column pressure 10 psi., injector temperature of 220° C., detector temperature of 300° C., argon carrier gas. Temperature program: Initial temperature 100° C., hold for 2 min.; ramp 1: 2° C./min. to 160° C.; ramp 2: 10° C./min. to 210° C.; hold for 2 min. Retention time $R_t$ for 4-methoxy styrene=20.5 mins. for branched aldehydes=33.3 mins, for linear aldehyde=36.0 mins. Retention time $R_t$ for 4-bromo styrene=19.3 mins. for branched aldehydes=35.4 mins. for linear aldehyde=38.5 mins. Retention time $R_t$ for 4-iso-butyl styrene=20.7 mins. for branched aldehydes=32.6 mins. for linear aldehyde=37.1 mins. Retention time $R_t$ for 4-tertbutyl styrene=19.9 mins. for branched aldehydes=33.3 mins. for linear aldehyde=36.2 mins. Retention time $R_t$ for 4-acetoxy styrene=30.0 mins. for branched aldehydes=32.9 mins. for linear aldehyde=38.44 mins. Retention time $R_t$ for 4-chloro styrene=14.4 mins. for branched aldehydes=31.4 mins. for linear aldehyde=36.0 mins. Retention time $R_t$ for 4-vinylbenzonitrile=28.3 mins. for branched aldehydes=37.0 mins. for linear aldehyde=38.5 mins. Retention time $R_t$ for Allyl benzene=8.4 mins. for branched aldehydes=24.3 mins. for linear aldehyde=29.2 mins.

Example 3

Hydroformylation of 1-Octene Using Fe Catalyst

Hydroformylation of 1-octene was performed in a stainless steel autoclave (450 mL) equipped with pressure regulator and a safety valve. In a glove box the vials were charged with $[(Ph_3P)_2—N]^+[HFe(CO)_4]^-$ (0.0055 g, 1 eq.), $PPh_3$ (0.0050 g, 2.5 eq.), dry MeOH (1 ml), 1-octene (0.12 ml, 100 eq.) along with Teflon stirring bars. Before starting the catalytic reactions, the charged autoclave was purged three times with syngas ($CO:H_2=1:1$) and then pressurized to 30 bar syngas pressure. The autoclave was heated at 100° C. in an oil bath for 24 hours. After catalysis, the autoclave was cooled to 0° C., and excess gas was vented. The conversion and regioselectivity were determined by GC using mesitylene as an internal standard. GC method for 1-octene is as under:

Column used: HP-5 (30 m*0.25 mm*320 μm), Split ratio 30:1, Inlet temperature 260° C., Column pressure 10 psi, Temperature program: started at 1) 70° C., hold for 1 min 2) 4° C. to 120° C. 3) 10° C. to 250° C. 4) 20° C. to 320° C. hold for 2 mins.

FID temperature: 330° C.

Result is shown in following table:

| Retention time | Area | Area % | Height | Height % |
|---|---|---|---|---|
| 2.775 | 10795405 | 16.40 | 3003949 | 19.60 |
| 7.113 | 16886492 | 25.65 | 4650727 | 30.35 |
| 8.275 | 38156662 | 57.95 | 7667703 | 50.04 |
| Totals | 65838559 | 100.00 | 15322379 | 100.00 |

Example 4

Acetic Acid Promoted Iron Catalyzed Hydroformylation

Acetic acid promoted hydroformylation of olefins 1-hexene, styrene, 4-methyl styrene, 4-methoxy styrene and 4-bromo styrene was performed with some modification as under. In a typical hydroformylation experiment a stainless steel autoclave (450 mL) equipped with 50 ml high pressure liquid charging chamber, pressure regulator and a safety valve was used. Individual vials were charged with metal precursor $\{[HFe(CO)_4]^-[PNP]+(5.5$ mg, 0.0077 mmol)$\}$, triphenyl phosphine and stirring bars in a glove box. The vials were transferred to a wide neck Schlenk container and methanol (1 ml), substrate (100 equiv.), and acetic acid was added. The vials were immediately transferred to autoclave and the autoclave was purged three times with syngas ($CO:H_2=1:1$) before pressurizing it to the desired pressure. Suitable temperature and pressure was maintained during the reaction. After completion of the reaction, the autoclave was cooled to 0° C., and excess gas was vented off in a well-ventilated fume-hood. The conversion and regio-selectivity were determined by gas chromatography (GC).

The results of acetic acid promoted iron $\{[HFe(CO)_4]–[PPN]+\}$ catalyzed hydroformylation 1-hexene, styrene, 4-methoxy styrene and 4-methyl styrene are presented in table 3 below:

TABLE

Acetic acid promoted iron (1) catalyzed hydroformylation of 1-hexene, styrene, 4- methoxy styrene and 4-methyl styrene[a]

| Sr. No. | Substrate | AcOH (equiv.) b | $CO/H_2$ bars | Time (h) | Conv. (%)c | L:Bc |
|---|---|---|---|---|---|---|
| 1 | 1-hexene | 1 | 20 | 16 | 49 | 72:28 |
| 2 | 1-hexene | 2 | 20 | 16 | 25 | 73:27 |
| 3 | 1-hexene | 5 | 20 | 16 | 1 | NA |
| 4 | styrene | 1 | 20 | 24 | 94 | 14:76 |
| 5 | 4-methoxy styrene | 1 | 20 | 24 | 32 | 16:84 |
| 6 | 4-methyl styrene | 1 | 20 | 24 | 64 | 16:84 |

TABLE-continued

Acetic acid promoted iron (1) catalyzed hydroformylation of 1-hexene, styrene, 4- methoxy styrene and 4-methyl styrene$^a$

| Sr. No. | Substrate | AcOH (equiv.) b | CO/H$_2$ bars | Time (h) | Conv. (%)c | L:Bc |
|---|---|---|---|---|---|---|
| 7 | 4-methoxy styrene | 1 | 20 | 24 | 80 | 8:92 |

$^a$Conditions: 1-0.0077 mmol, Ligand/Metal: 2.5, Sub/Fe: 100, Solvent: 1 ml Methanol, NA: Not determined;
b equivalent of acetic acid as compared to the catalyst,
cDetermined by GC.

ADVANTAGES OF THE INVENTION

1) Cheap iron metal is used.
2) Cheap and commercially available ligands have been used.
3) Hydroformylation is catalyzed under mild conditions.
4) Hydroformylation of 4-isobutyl styrene followed by its oxidation leads to Ibuprofen, a very popular, NSAID (Non-steroidal anti-inflammatory drug).

The invention claimed is:

1. A one-step process for hydroformylation of olefins, comprising
charging iron precursor, ligand, substrate, and solvent in a reaction vessel followed by pressurizing the reaction mixture with syngas (CO/H$_2$) under constant stirring at temperature in the range of 70 to 100° C. for a period in the range of 16 to 48 hrs to produce a desired aldehyde compound,
wherein the conversion of said olefin is in the range of 40 to 99%, the ligand is selected from a group consisting of monodentate ligands of phosphines and phosphites and the iron precursor is [HFe(CO)$_4$]$^-$.

2. The process as claimed in claim 1, wherein the process comprises addition of an acid to the reaction mixture.

3. The process as claimed in claim 2, wherein the acid is at least one selected from the group consisting of acetic acid and formic acid.

4. The process as claimed in claim 1, wherein the pressure of the syngas (CO/H$_2$) is in the range of 10 to 30 bars.

5. The process as claimed in claim 1, wherein the ligand is selected from the group consisting of Triphenylphosphine (PPh$_3$) and Triphenyl phosphite [P(OPh)$_3$].

6. The process as claimed in claim 1, wherein the solvent is selected from the group consisting of methanol, ethanol, isopropyl alcohol, and acetic acid.

7. The process as claimed in claim 1, wherein the olefin is at least one selected from the group consisting of linear olefin, terminal olefin, and internal olefin.

8. The process as claimed in claim 7, wherein the olefin is selected from the group consisting of 1-hexene, 1-octene, 1-decene, 1-dodecene, 1-octadecene, trimethoxy(vinyl)silane, trimethyl(vinyl)silane, cardanol, 2, 3-dihydrofuran, allyl malonic acid, styrene, 4-methyl styrene, 4-iBu-styrene, 4-tBu-styrene, 4-methoxy styrene, 4-acetoxy styrene, 4-bromo styrene, 4-chloro styrene, 4-vinylbenzonitrile, 4-vinylbenzoic acid, and allyl benzene.

9. The process as claimed in claim 1, wherein the reaction is carried out in a batch mode or a continuous mode of operation.

\* \* \* \* \*